(12) United States Patent
Wang et al.

(10) Patent No.: US 11,986,263 B2
(45) Date of Patent: May 21, 2024

(54) POWER MECHANISM AND SLAVE OPERATING DEVICE

(71) Applicant: Shenzhen Edge Medical CO., Ltd., Guangdong (CN)

(72) Inventors: Jianchen Wang, Shenzhen (CN); Yuanqian Gao, Shenzhen (CN)

(73) Assignee: Shenzhen Edge Medical CO., Ltd., Guangdong (CN)

( * ) Notice: Subject to any disclaimer, the term of this patent is extended or adjusted under 35 U.S.C. 154(b) by 908 days.

(21) Appl. No.: 16/979,268

(22) PCT Filed: Mar. 11, 2019

(86) PCT No.: PCT/CN2019/077648
§ 371 (c)(1),
(2) Date: Sep. 9, 2020

(87) PCT Pub. No.: WO2019/174543
PCT Pub. Date: Sep. 19, 2019

(65) Prior Publication Data
US 2020/0397521 A1  Dec. 24, 2020

(30) Foreign Application Priority Data

Mar. 12, 2018 (CN) .......................... 201810199278.4
Mar. 23, 2018 (CN) .......................... 201810244035.8
Jun. 22, 2018 (CN) .......................... 201810649286.4

(51) Int. Cl.
*A61B 34/37* (2016.01)
*A61B 17/00* (2006.01)
*A61B 34/00* (2016.01)

(52) U.S. Cl.
CPC ........ *A61B 34/37* (2016.02); *A61B 17/00234* (2013.01); *A61B 34/70* (2016.02); *A61B 2560/04* (2013.01)

(58) Field of Classification Search
CPC ... A61B 34/37; A61B 34/70; A61B 17/00234; A61B 2560/04
See application file for complete search history.

(56) References Cited

U.S. PATENT DOCUMENTS

2016/0374767 A1* 12/2016 Diolaiti .................. A61B 34/71
700/245

FOREIGN PATENT DOCUMENTS

| CN | 102014759 A | 4/2011 |
| CN | 103431913 A | 12/2013 |
| CN | 104688281 A | 6/2015 |
| CN | 205219114 U | 5/2016 |
| CN | 105997254 A | 10/2016 |

(Continued)

*Primary Examiner* — Catherine M Voorhees
*Assistant Examiner* — Roland Dinga
(74) *Attorney, Agent, or Firm* — ScienBiziP, P.C.

(57) ABSTRACT

The application discloses a power mechanism and a slave operating device. The power mechanism, for connecting to an operating arm, includes a body and a power mechanism. A side surface of the body defines a mounting groove. The mounting groove passes through a bottom surface of the body. A distal end of the operating arm is located out of the mounting groove. The power portion is disposed on the body for connecting to the operating arm and providing power for the operating arm. The above power mechanism enables the operating arm to be simpler and more rapid to install.

18 Claims, 14 Drawing Sheets

(56) References Cited

FOREIGN PATENT DOCUMENTS

CN 108888345 A 11/2018
JP 2009201607 A 9/2009

* cited by examiner

POWER MECHANISM AND SLAVE OPERATING DEVICE

FIELD

The subject matter herein generally relates to surgical systems, in particular to a power mechanism and a slave operating device.

BACKGROUND

Minimally invasive surgery refers to a surgical method of performing a procedure in a human body cavity using modern medical instruments and related devices such as laparoscopes, thoracoscopes, and the like. Compared with the traditional surgery mode, minimally invasive surgery has the advantages of being small in trauma, light in pain, fast in recovery, and the like.

With advances in science and technology, minimally invasive surgical robot technologies are increasingly mature and widely used. A minimally invasive surgical robot typically includes a master console and a slave operating device. The surgeon controls the slave operating device to perform surgical operations by operating the master console. The slave operating device typically includes a power mechanism and an operating arm removably mounted to the power mechanism. The operating arm is used for extending into the body to perform a surgical operation. However, disassembly or assembly of the operating arm of the slave operating device is complicated and is not easy to use.

SUMMARY

In view of the above problems, the present disclosure provides a power mechanism for enabling an operating arm to be disassembled or assembled, and a slave operating device using the power mechanism are provided.

A power mechanism for connecting to the operating arm includes:
- a body, a side surface of the body defining a mounting groove, the mounting groove passing through the bottom surface of the body to enable the operating arm move from the side surface into the mounting groove, and a distal end of the operating arm located out of the mounting groove; and
- a power portion, disposed on the body, for connecting to the operating arm and providing power for the operating arm.

A slave operating device includes:
- a power mechanism, the power mechanism including a body and a power portion, a side surface of the body defining a mounting groove, the mounting groove passing through the bottom surface of the body, the power portion disposed on the body;
- an operating arm connected to the power portion and passing through the mounting groove to enable the operating arm move from the side surface into the mounting groove, and distal end of the operating arm located out of the mounting groove The operating arm is connected to the power portion and penetrates through the mounting groove, so that the operating arm is translated from the side surface into the mounting groove, and the distal end of the operating arm is located outside the mounting groove.

The slave operating device with the above power mechanism makes it easier and faster to install the operating arm.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings and the following descriptions show merely some embodiments of the present invention, and a person of ordinary skill in the art may still derive other drawings from these accompanying drawings without creative efforts.

DETAILED DESCRIPTION

Figure 1:
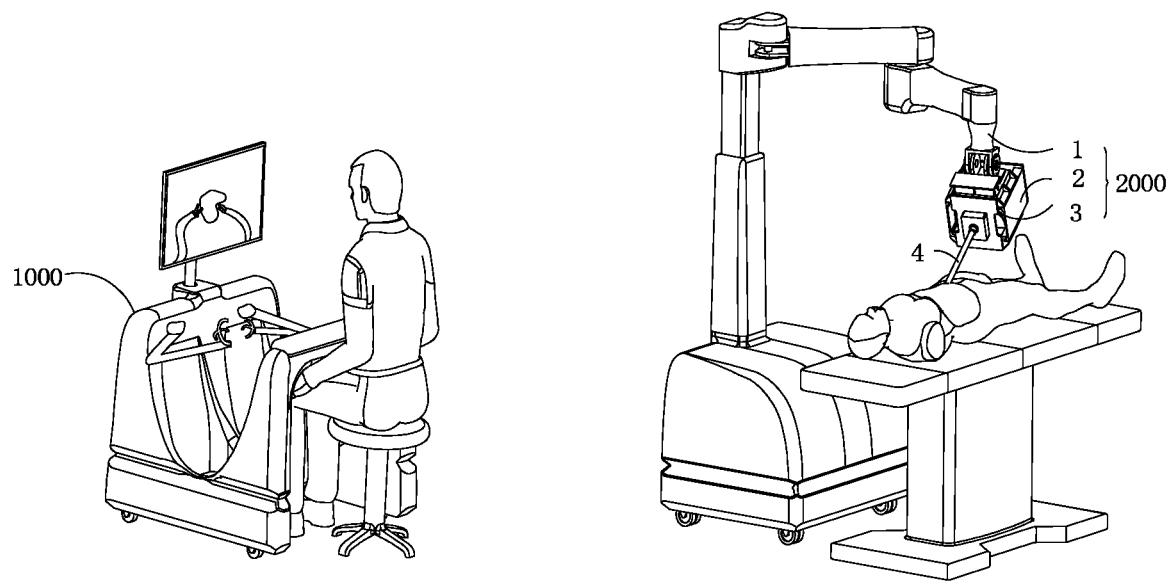
FIG. 1 is a structural schematic view of an embodiment of a surgical robot according to the present disclosure.

Implementations of the disclosure will now be described, by way of embodiments only, with reference to the drawing. The disclosure is illustrative only, and changes may be made in the detail within the principles of the present disclosure. It will, therefore, be appreciated that the embodiments may be modified within the scope of the claims.

For ease of understanding of the present application, the present application will be described more fully hereinafter with reference to the associated drawings. Preferred embodiments of the present application are set forth in the accompanying drawings. This application may, however, be embodied in many different forms and is not limited to the embodiments described herein. Rather, these embodiments are provided for the purpose of providing a more thorough and thorough understanding of the disclosure of the present application.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure. Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

Figure 2:
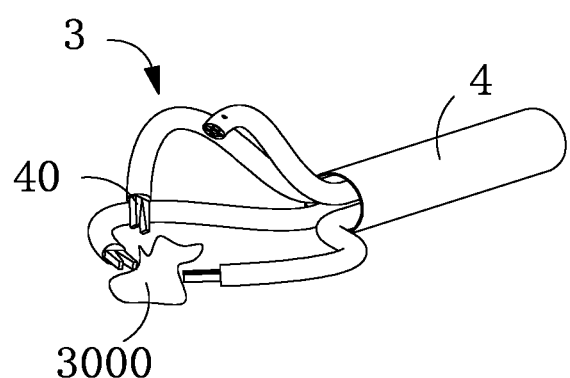
FIGS. 2 and 3 are partial schematic views of different embodiments of a slave operating device.
Figure 3:
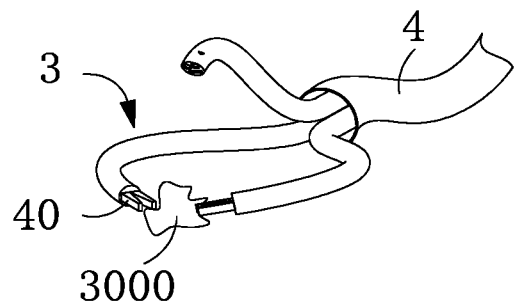

As shown in FIGS. 1-3, a structural schematic view of an embodiment of a surgical robot of the present application and a partial schematic view of different embodiments of the slave operating device are shown. The surgical robot includes a master console 1000 for sending control commands to the slave operating device 2000 according to the operation of the surgeon to control the slave operating device 2000. The master console 1000 is also used for displaying images acquired from the slave operating device 2000. The slave operating device 2000 is used for responding to the control commands sent by the master console 1000 and performing corresponding operations, and the slave operating device 2000 is also used for acquiring images in the human body.

Specifically, the slave operating device includes a mechanical arm 1, a power mechanism 2 disposed on the mechanical arm 1, an operating arm 3 disposed on the power mechanism 2, and a sleeve 4 sleeving the operating arm 3. The mechanical arm 1 is used for adjusting the position of the operating arm 3. The power mechanism 2 is used for driving the operating arm 3 to perform a corresponding operation. The operating arm 3 is used for extending into the human body and performing a surgical operation by the end effector located at the distal end of the operating arm, and/or acquiring images within the human body. As shown in FIG. 2 and FIG. 3, the operating arm 3 passes through the sleeve 4, and the end effector 40 extends out of the sleeve 4 and is driven by the power mechanism 2 to perform the operation. In FIG. 2, the part of the operating arm 3 located in the sleeve 4 is a rigid part. In FIG. 3, the part of the operating arm 3 located in the sleeve 4 is a flexible part, and the sleeve is bent with the flexible region. In another embodiment, the sleeve 4 may also be omitted, at which point the sleeve is not required.

In one embodiment, the operating arm 3 is a plurality of operating arms 3 disposed on the same power mechanism 2, and the distal ends of the plurality of operating arms 3 extend into the human body via an incision in the human body to move the end effectors 40 of the operating arm 3 to the vicinity of the lesion 3000 for a surgical operation. Specifically, the power mechanism has a plurality of power portions, and each power portion is connected to an operating arm. In another embodiment, the power mechanism is a plurality of power mechanisms 2. Each power mechanism 2 is provided with an operating arm 3, and the plurality of operating arms extend into the human body via one incision, and the plurality of power mechanisms 2 can be disposed on a mechanical arm 1 or on a plurality of mechanical arms 1. It should be noted that the plurality of operating arms 3 may also extend into the human body via a plurality of incisions. For example, there are two operating arms extending into each of the incisions, or there is one operating arm extending into each of the incisions.

In one embodiment, the slave operating device 2 further includes a trocar for penetrating the incision in the human body and fixedly disposed in the trocar, and the operating arm extends into the body via the trocar.

Figure 4:
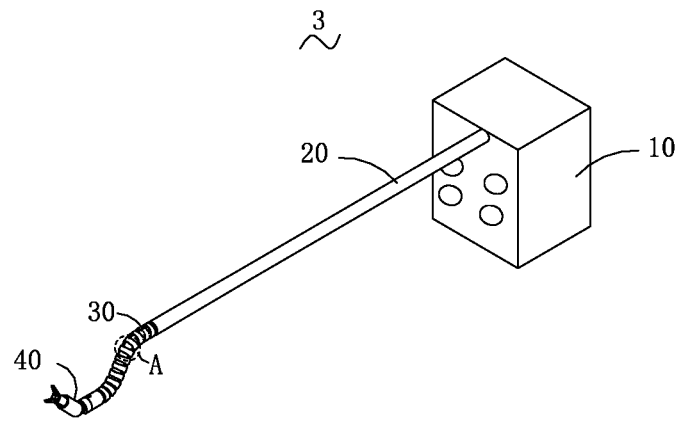
FIGS. 4 and 5 are schematic views of an embodiment of an operating arm and a partial and enlarged view of a portion A of the operating arm respectively.

As shown in FIG. 4, a structural schematic view of an embodiment of an operating arm 3 of the present application is shown. The operating arm 3 includes a driving mechanism 10, a connecting rod 20, a connecting unit assembly 30, and an end effector 40, which are sequentially connected. Wherein the power mechanism is connected to the driving mechanism 10 and provides power for the driving mechanism 10. The driving mechanism 10 is used for driving the connecting unit assembly 30 and the end effector 40, the connecting unit assembly 30 is used for changing the position and pose of the end effector 40, and the end effector 40 is used for performing a surgical operation. In another embodiment, the connecting rod 20 may also be omitted, at which point the connecting unit assembly is directly connected to the driving mechanism, and the connecting unit assembly passes through the sleeve 4 and/or the trocar.

Figure 5:
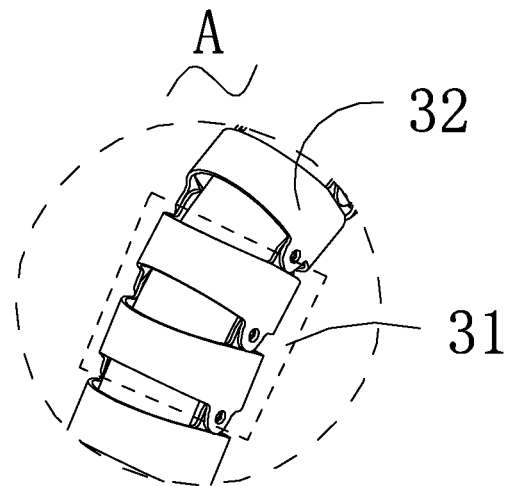

As shown in FIG. 5, the connecting unit assembly 30 includes a plurality of connecting units 32 which are sequentially connected, wherein at least two adjacent connecting units 32 form a rotatable joint assembly 31. In one embodiment, a plurality of connecting unit assemblies are connected via a driving wire so that a plurality of connecting units 32 form a rotatable joint assembly 31. In another embodiment, the plurality of connecting unit assemblies may also be connected by other connecting members. The connecting members and the connecting units form a joint assembly.

Figure 6:
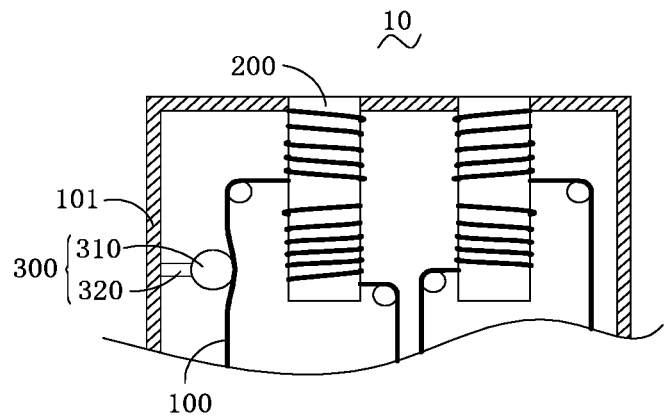
FIGS. 6 to 17 are structural schematic views of different embodiments of a driving structure of the operating arm.
Figure 7:
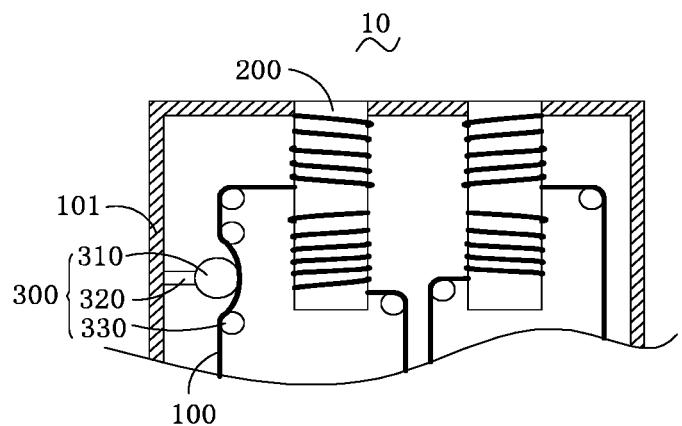

As shown in FIGS. 6 and 7, structural schematic views of different embodiments of the driving mechanism 10 are shown. The driving mechanism 10 includes a housing 101, a driving wire 100, a driving portion 200 and a tensioning portion 300. Wherein the driving wire 100 for driving the connecting unit assembly 30 is connected to the driving portion 200, and the connecting unit assembly 30, to drive the connecting unit assembly 30 to be bent, thereby adjusting the pose and the position of the end effector 40. The driving wire 100 for driving the end effector is connected to the end effector 40 and the driving portion 200, to drive the end effector 40 to be opened or closed, thereby performing the surgical operation. Specifically, the driving wire passes through the connecting rod 20 and extends to the connecting unit assembly 30 or the end effector 40, to drive the joint assembly 31 or the end effector 40 of the connecting unit assembly 30. The driving portion is disposed on the housing for driving the driving wire to move, thereby driving the connecting unit assembly 30 and the end effector 40. The tensioning portion 300 is disposed on the housing 101 for resisting against the driving wire 100 so as to tension the driving wire 100. In another embodiment, the driving wire for driving the end effector may be omitted, and the end effector does not need to be driven. According to the driving mechanism, the driving wire can be prevented from loosening, to enable the driving mechanism to drive the connecting unit assembly and the end effector to move more accurately.

As shown in FIG. 6, the tensioning portion 300 includes a resisting portion 310 and an adjusting portion 320 connected to the resisting portion 310. Wherein the resisting portion 310 resists against the driving wire 100. The adjusting portion 320 is disposed on the housing for automatically adjusting the position of the resisting portion 310 so that the driving wire is further prevented from loosening, and the driving precision can still be ensured after long-time use.

As shown in FIG. 7, the tensioning portion 300 further includes auxiliary resisting portions 330 disposed on the housing 101. The auxiliary resisting portions 330 cooperates with the resisting portion 310 to resist against the driving wire 100, so as to tension the driving wire 100. Specifically, the auxiliary resisting portions 330 are disposed adjacent to the resisting portion 310. The resisting portion 310 for tensioning driving wire 100 and the auxiliary resisting portion 330 resist against the driving wire in the opposite directions, that is, the auxiliary resisting portion and the resisting portion 310 resist against the driving wire 100 in the opposite direction. The number of the auxiliary resisting portions 330 is two and the resisting portion 310 is located between the two auxiliary resisting portions. In another embodiment, the number of the auxiliary resisting portions may be other numbers, such as one. The auxiliary resisting portion cooperates with the resisting portion to tension the driving wire, so that the movement distance of the resisting portion can be shortened, and the internal structure of the driving portion is more compact.

Moreover, the resisting portion 310 has a pulley whose movement direction is the same as the resisting direction, that is, the movement direction of the resisting portion is perpendicular to the movement direction of the driving wire located in the resisting portion. In this way, on one hand, the driving wire can be tensioned, and on the other hand, the resistance can be reduced when the driving wire moves. In another embodiment, the resisting portion may be other structures, for example, the resisting portion has a curved end portion that resists against the driving wire.

Figure 8:
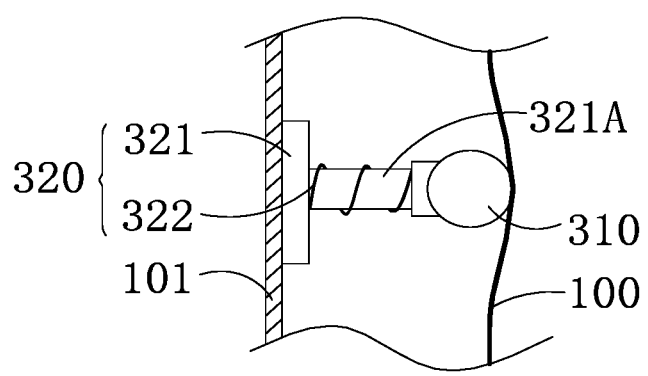

As shown in FIGS. 8-11, partial structure views of different embodiments of the driving mechanisms are shown. In one embodiment, the adjusting portion 320 includes a body 321 and an elastic unit 322. As shown in FIG. 8, the elastic direction of the elastic unit 322 is parallel to the movement direction of the resisting portion 310. Specifically, the body 321 is a T-shaped body and is disposed on the housing 101. The body has a connecting rod 321A. The elastic unit 322 is connected to the resisting portion 310, and the connecting rod 321A is sleeved with the elastic unit 322 and resisting portion 310 sequentially, thereby enabling the resisting portion to move along the connecting rod 321A.

Figure 9:
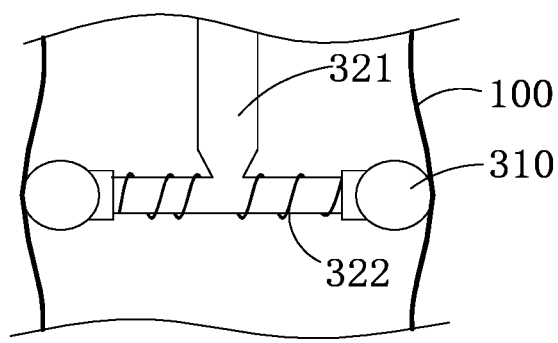
Figure 10:
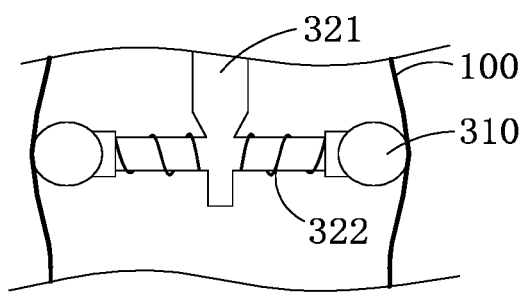
Figure 11:
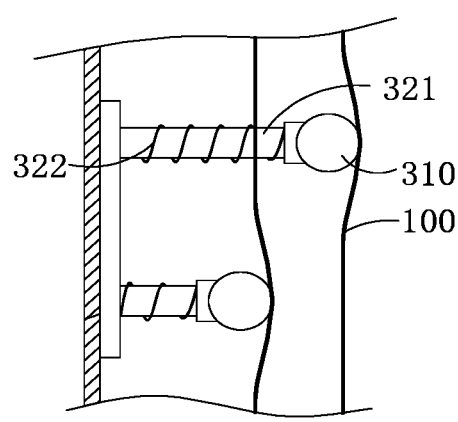

In another embodiment, the tensioning portion 300 may also include two resisting portions 310, and each of the resisting portions 310 resists against one of the driving wires 100. As shown in FIG. 9, the two resisting portions 310 are respectively disposed at opposite ends of the elastic unit 322 to enable one tensioning portion 300 to tension the two driving wires. In addition, as shown in FIGS. 10 and 11, there are two elastic units 322, and each elastic unit 322 is provided with one resisting portion 310. The elastic directions of the two elastic units 322 in FIG. 10 are the same, and the two elastic units 322 resist against the corresponding driving wires in different directions. The two elastic units 322 in FIG. 11 are arranged side by side, the elastic directions of the two elastic units are the same, and the elastic units 322 resist against the corresponding driving wires respectively in the same direction.

Figure 12:
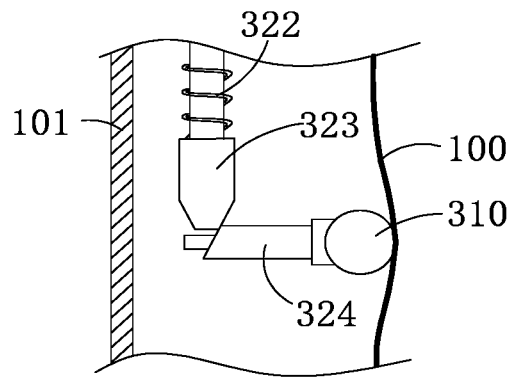

In the embodiment shown in FIG. 12, the elastic direction of the elastic unit 322 is perpendicular to the movement direction of the resisting portion 310. Specifically, the adjusting portion 320 includes a first adjusting member 323, a second adjusting member 324, and an elastic unit 322, wherein the first adjusting member 323 is connected to the elastic unit 322 and has a first inclined surface. The second adjusting member 324 is connected to the resisting portion 310 and has a second inclined surface. The first inclined surface of the first adjusting member resists against the second inclined surface of the second adjusting member, so that the first adjusting member drives the resisting portion 310 to move by the second adjusting member 324 under the action of the elastic force. Wherein the elastic direction of the elastic unit 322 is perpendicular to the movement direction of the resisting portion 310, and the second adjusting member 324 is slidably disposed on the housing in the movement direction. For example, the housing defines a groove, and the second adjustment member has a sliding portion slidably disposed within the groove.

Figure 13:
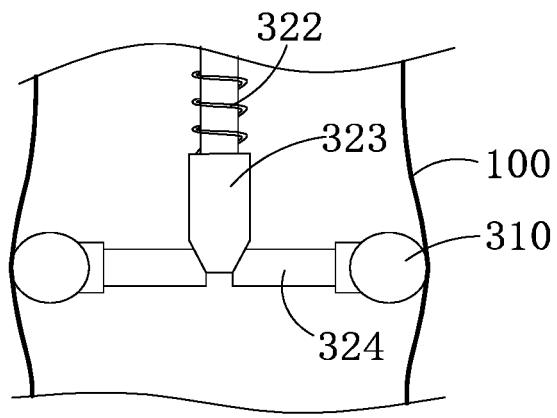

In the embodiment shown in FIG. 13, both of the number of the second adjusting members 324 and the resisting portion 310 are two. Each resisting portion is disposed on a corresponding second adjusting member 324. The first adjusting member simultaneously drives two second adjusting members to move, and the movement directions of the two second adjusting members 324 are opposite.

In another embodiment, only the first adjustment member or the second adjustment member may have an inclined surface. Alternatively, the elastic unit may be omitted, at which point the adjusting portion is manually adjusted. Alternatively, the elastic direction of the elastic unit and the resisting direction may also at an acute angle or an obtuse angle.

As shown in FIGS. 9-11 and 13, the tensioning portion 300 may simultaneously tension a plurality of driving wires via a plurality of resisting portions of the tensioning portion, and may also resist against a plurality of driving wires via one resisting portion of the tensioning portion. When one tensioning portion resists against the plurality of driving wires, the plurality of driving wires tensioned by the tensioning portion 300 are similar in degree of wear during operation, thereby enabling the tensioning effect to be better. For example, when a joint assembly is driven by a plurality of driving wires, the plurality of driving wires may be tensioned by the same tensioning portion 300. As another example, when a plurality of joint assemblies is coupled, the driving wires for driving the coupled joint assemblies are tensioned via the same tensioning portion 300.

In the above embodiment, the plurality of driving wires 100 for driving the same joint assembly or the plurality of driving wires 100 for driving the coupling joint assembly is similar in degree of wear during operation of the operation arm. Therefore, due to tensioning of the tensioning portion 300, space can be saved, and the tension degree of the driving wires can be similar to enable the connecting unit assembly or the end effector of the operation arm can be better controlled.

It should be noted that a driving wire may be tensioned by a plurality of tensioning portions that are located on different parts of the driving wire, and the movement direction of the plurality of parts of the driving wire is different. In this way, when the transmission direction of a driving wire is changed via the transmission wheel, the driving wire can still be tensioned better.

Figure 14:
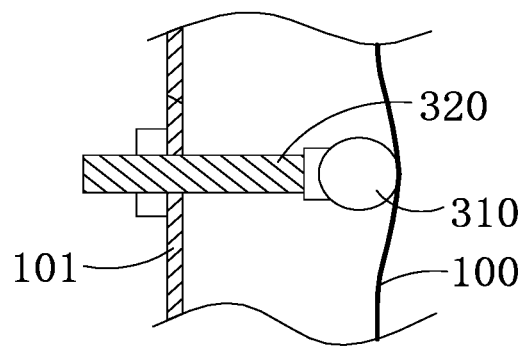

In one embodiment, the driving wire is tensioned by the driving mechanism in a manual manner. For example, the elastic unit 322 in each of the above embodiments is omitted. Specifically, as shown in FIG. 14, the tensioning portion 300 is screwed to the housing 101 by a threaded fastener. Specifically, the adjusting portion 320 has screw threads, and the adjusting portion 320 cooperates with a nut to adjust the position of the body relative to the housing 101, thereby adjusting the position of the resisting portion 310. It should be noted that the embodiments described above may also be implemented in conjunction with the embodiment shown in FIG. 14 to achieve manual and automatic adjustment.

Figure 15:
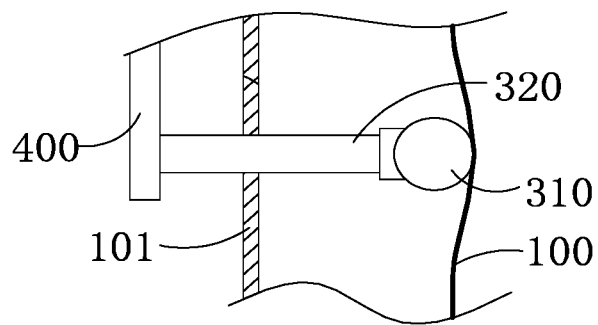
Figure 16:
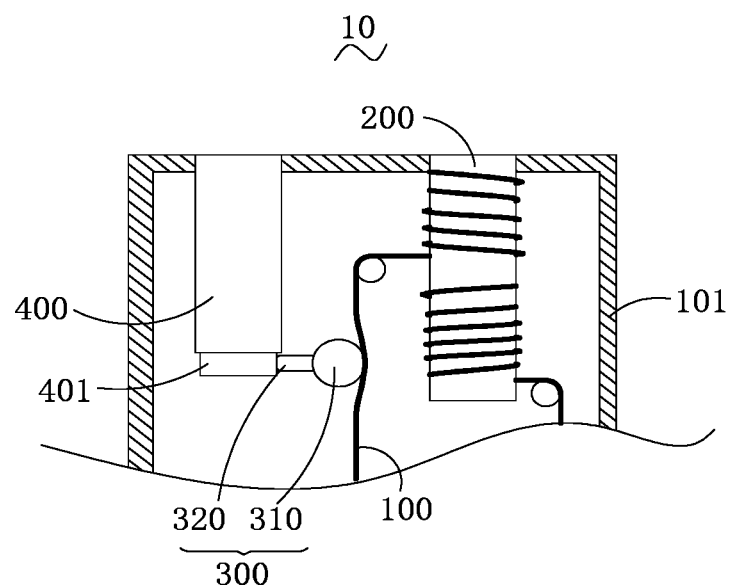
Figure 17:
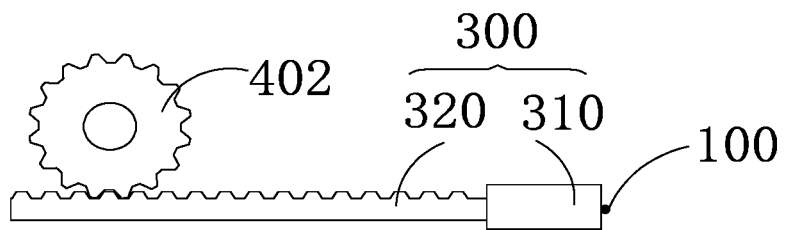

In addition, as shown in FIGS. 15-17, the tensioning portion 300 may also be driven by the tension driving portion 400 to tension the driving wire. Specifically, the driving mechanism 10 further includes a tension driving portion 400 connected to the tensioning portion 300 for driving the tensioning portion 300, wherein the tension driving portion 400 is connected to the adjusting portion 320 of the tensioning portion 300 and adjusts the position of the resisting portion 310 by the driving adjusting portion 320. At this point, it should be noted that the adjusting portion 320 may include the elastic unit 322 or not include the elastic unit 322.

As shown in FIG. 15, the tension driving portion 400 is disposed out of the housing 101. The adjusting portion 320 passes through the housing 101 and is capable of sliding relative to the housing 101. The adjusting portion 320 moves with the tension driving portion 400. In this embodiment, the tension driving portion 400 and the tensioning portion 300 both move along a straight line, and the movement directions of them are the same. Moreover, the tension driving portion 400 is detachably connected to the adjusting portion 320 to be convenient for the replacement of the operating arm.

In the embodiment shown in FIG. 16, the adjusting portion 320 and the tension driving portion 400 are both disposed within the housing 101. Wherein the tension driving portion 400 rotates about its axis and drives the adjusting portion 320 to move along a straight line, thereby adjusting the position of the resisting portion 310. Specifically, the tension driving portion 400 and the adjusting portion 320 form a cam mechanism, wherein the tension driving portion 400 has a cam 401, and the adjusting portion 320 resists against the curved surface of the cam 401 and moves along a straight line. In this embodiment, the movement direction of the resisting portion 310 is the same as the movement direction of the adjusting portion 320. In other embodiments, the movement direction of the resisting portion may also be different from the movement direction of the adjusting portion 320.

In another embodiment, the tension driving portion 400 and the adjusting portion 320 may also form a gear rack mechanism, as shown in FIG. 17, the tension driving portion 400 has a gear 402, the adjusting portion 320 has a rack matched with the gear 402, each tension driving portion may be connected to a plurality of adjusting portions. For example, one tensioning portion is connected to two adjusting portions, and the two adjusting portions are respectively located on opposite sides of the gear and engage with the gear.

In one embodiment, the driving mechanism maintains the tension of the driving wire via the tension driving portion. For example, a force sensor is placed on a portion of the tensioning portion resisting against the driving wire. The force sensor is used for feeding back the resisting force to enable the tension driving portion to maintain the tension of the driving wire. Specifically, the operating arm has a host for controlling the operation of the operating arm. The host is used for acquiring the feedback resisting force and defining a predetermined value of a resisting force. When the feedback resisting force is greater than the predetermined value, the driving wire is tensioned excessively. At this moment, the resisting portion is adjusted by the tension driving portion to reduce the resisting force generated by the resisting portion resisting applied to the driving wire. When the feedback resisting force is less than the predetermined value, the driving wire relaxes. At this time, the resisting portion is adjusted by the tension driving portion to increase the resisting force of the resisting portion applied to the driving wire.

In one embodiment, the tension driving portion 400 adjusts the tensioning portion 300 according to the pose of the connecting unit assembly. Wherein the connecting unit assembly has an angle sensor for feeding back the bending angle information, and the tension driving portion 400 adjusts the tensioning portion 300 according to the bending angle information. Specifically, the connecting unit assembly includes a plurality of joint assemblies arranged in sequence. The angle sensor is disposed on at least one of the joint assemblies to detect the bending angle of the joint assembly and to obtain and feedback the bending angle information. The operating arm has a host for controlling the operation of the operating arm, and the host is used for acquiring the feedback bending angle information and acquiring predetermined rotation angle information in real time. When it is detected that the bending angle of the joint assembly is smaller than the acquired predetermined rotation angle, the driving wire relaxes. At this time, the resisting portion 310 is adjusted by the tension driving portion 400 to tension the driving wire. When it is detected that the bending angle of the joint assembly is greater than the predetermined rotation angle, the driving wire is judged to be tightened excessively. At this time, the resisting portion 310 is adjusted by the tension driving portion 400 to relax the driving wire. The predetermined rotation angle is acquired in real time according to the operation of the surgeon. The host controls the driving portion to drive the joint assembly to rotate according to the predetermined rotation angle, and the actual rotation angle of the joint assembly is the bending angle.

Figure 18:
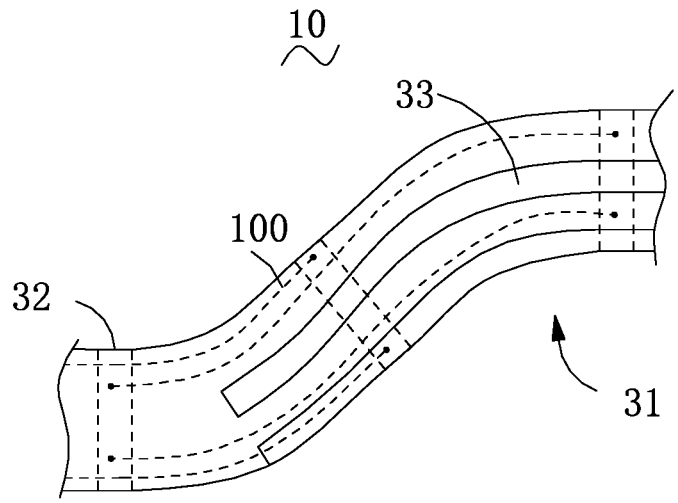
FIG. 18 is a structural schematic view of an embodiment of a connecting unit assembly of the operating arm.

As shown in FIG. 18, the connecting unit assembly 30 has a pose sensor 33 for feeding back pose information, and the tension driving portion 400 adjusts the tensioning portion 300 according to the pose information. In this embodiment, the pose sensor 33 is strip shaped. The pose sensor 33 extends in the extending direction of the connecting unit assembly 30 and covers the at least one joint assembly 31. The pose sensor 33 is used for acquiring pose information of the joint assembly 31 according to the stress distribution of each region thereof. At least one of the joint assemblies has a plurality of pose sensors. The distance between each proximal end of the plurality of pose sensors and the proximal end of the detected joint assembly is equal, that is, the distance between each proximal end of the plurality of pose sensors and the connecting unit located on the proximal end of the detected joint assembly is equal. The distance between each distal end of the plurality of pose sensors and the distal end of the joint assembly is equal to each other, that is, the distance between each distal end of the plurality of pose sensors and the connecting unit located on the distal end of the joint assembly is equal to each other.

In the embodiment, the operating arm has a host that controls the operation of the operating arm. The host obtains the desired pose information after the rotation of the control joint assembly 31 according to the predetermined rotation angle information acquired in real time and compares the desired pose information with the pose information fed back by the pose sensor, thereby adjusting the tensioning portion 300. Wherein the host is located in the master console. Wherein the predetermined rotation angle information is acquired in real time according to the operation of the surgeon. The host obtains the desired pose information according to the predetermined rotation angle information. The desired pose information is the coordinate information of the desired position of each region of the joint assembly 31. The feedback pose information is the coordinate information of the actual position of each region of the joint assembly 31, and each position corresponds to each of the acquired desired pose information. In another embodiment, the host can also obtain the bending angle information according to the fed back pose information, and compares the bending angle information with the acquired predetermined rotation angle information, thereby adjusting the tensioning portion 300. Alternatively, the host can directly obtain the desired pose information.

It should be noted that in the embodiments described above, the sensor feeds the acquired information back to the host. The host processes the feedback information and controls the tension driving portion 400 to adjust the tensioning portion 300. Wherein the host can be located on the slave operating device. For example, the driving portion of the operating arm on the master operating console.

Figure 19:
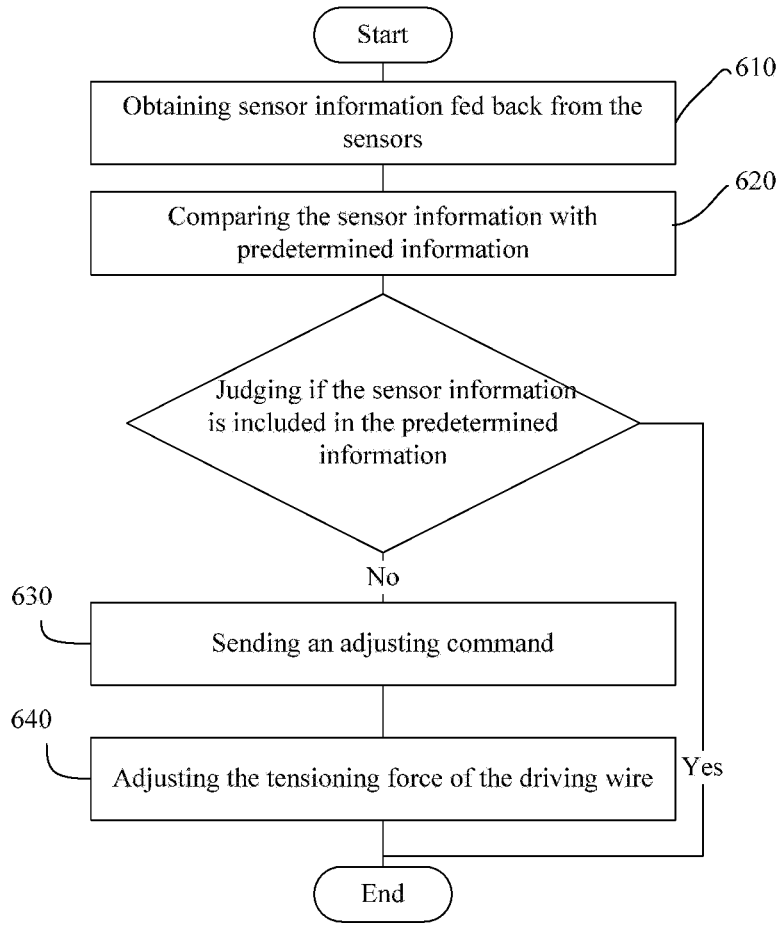
FIG. 19 is a flow view of an embodiment of a tensioning method of the driving structure of the operating arm.

As shown in FIG. 19, the tensioning method of the driving mechanism includes the following steps.

In step S610, sensor information fed back by the sensor is obtained.

Wherein the sensor information may be the force information fed back by the pressure sensor. Specifically, the sensor is disposed in a region where the tensioning portion resists against the driving wire for feeding back the resisting force information.

The sensor information may also be bending angle information fed back by the angle sensor. Specifically, the angle sensor is placed on the joint assembly of the connecting unit assembly for feeding back the bending angle of the joint assembly detected by the angle sensor, wherein the bending angle is the actual rotation angle of the joint assembly when the joint assembly rotates according to the acquired preset rotation angle information.

The sensor information may also be pose information fed back by the pose sensor, or bending angle information obtained from the pose information. The method for obtaining the bending angle information according to the pose information includes the following steps.

(1) First pose information corresponding to the current pose of the joint assembly is obtained. Specifically, the current pose information is obtained before the joint assembly rotates according to the predetermined rotation angle information.

(2) Second pose information is obtained after the joint assembly changes the pose. Specifically, after the predetermined rotation angle information is acquired, the joint assembly rotates according to the information, thereby changing the pose of the joint assembly and obtaining the second pose information after the joint assembly changes the pose.

(3) Bending angle information is obtained according to the first pose information and the second pose information.

It should be noted that after step (2) or step (3), before obtaining a next predetermined rotation angle information, a pose is obtained after the joint assembly rotates according to a previous rotation angle information and the pose is updated as a current pose of the joint assembly in the next cycle. That is, the second pose in the previous cycle is the first pose in the next cycle. The pressure sensor, the angle sensor, and the pose sensor may be the sensors of the aforementioned embodiments, and the relevant contents of the sensors are not repeated here.

In step S620, the sensor information is compared with the predetermined information.

When the sensor information is the resisting force information, the predetermined information is the predetermined resisting force information. When the sensor information is the bending angle information, the predetermined information is the obtained predetermined rotation angle information. When the sensor information is pose information, the predetermined information is the desired pose information. The desired pose information is the pose information of the joint assembly after the joint assembly rotates according to the predetermined rotation angle information. The desired pose information is calculated to be obtained according to the obtained predetermined rotation angle information. Alternatively, the pose information of the joint assembly may also be directly obtained.

It should be noted that the predetermined information can be pre-processed predetermined information. For example, the predetermined rotation angle information, obtained according to the operation of the surgeon, is pre-processed to compensate for the rotation angle information. Alternatively, the predetermined information is not pre-processed. For example, the predetermined angle information is directly obtained according to the operation of the surgeon.

The sensor information may also include at least two of the above information. For example, the sensor information includes resisting force information and bending angle information. Each sensor information is compared to the corresponding predetermined information. All of the predetermined information can be pre-processing predetermined information, or part of the predetermined information may be pre-processing predetermined information, or none of the predetermined information is pre-processed.

In step S630, if the sensor information is not within the range of the predetermined information, the adjusting command is sent out. If the sensor information is within the range of the predetermined information, it is not necessary to adjust the tension of the driving wire. The predetermined information may be a specific value and may be a range of intervals.

Specifically, if the sensor information is less than the predetermined information, an adjusting command for increasing the tensioning force is sent out. The sensor information is less than the predetermined information, and when the sensor information is the resisting force information, the resisting force on the driving wire is less than the predetermined resisting force. When the sensor information is the bending angle information, the bending angle of the rotation of the joint assembly is smaller than the obtained predetermined rotation angle information. When the sensor information is pose information, the deviation distance of the joint assembly is smaller than the desired deviation distance. That is, the distance between the coordinates of the joint assembly before and after rotation of the joint assembly is less than the desired distance.

It should be noted that if the sensor information includes a plurality of information, the adjusting command for increasing the tensioning force is sent out when the plurality of information is less than the predetermined information.

If the sensor information is greater than the predetermined information, the adjusting command for reducing the tensioning force is sent out. This is similar to the relevant content when the sensor information is less than the preset information and is not repeated here.

It should be noted that in one embodiment, the adjusting command may be sent out only when the sensor information is less than the preset information. The adjusting command is not sent out when the information is greater than the preset information, at this time, the adjustment is not needed. Alternatively, the adjusting command may be sent only when the sensor information is greater than the preset information, and no adjustment command is sent when the information is less than the preset information.

In step S640, the tensioning force of the driving wire is adjusted according to the adjusting command.

Specifically, as shown in FIG. 16 and FIG. 17, the tension driving portion rotates about the axis of the tension driving portion to drive the tensioning portion to move linearly and to adjust the position of the resisting portion, thereby adjusting the tensioning force of the driving wire. Alternatively, as shown in FIG. 15, the tension driving portion pushes the driving portion linearly to adjust the position of the resisting portion, thereby adjusting the tensioning force of the driving wire.

In one embodiment, after step S640, the steps S610 and S620 are executed again to detect whether the tensioning force meets the requirement, and if not, the step S630 or the step S640 continues to adjust the tensioning force until the tensioning force meets the requirement.

Figure 20:
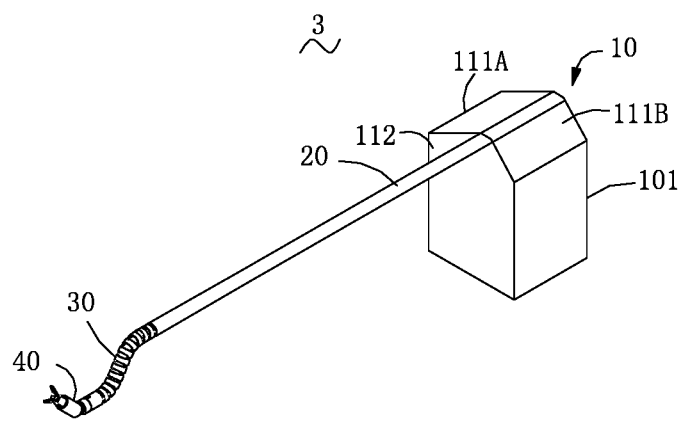
FIGS. 20 to 29 and FIGS. 31-32 are structural schematic views of different embodiments of the operating arm respectively.
Figure 21:
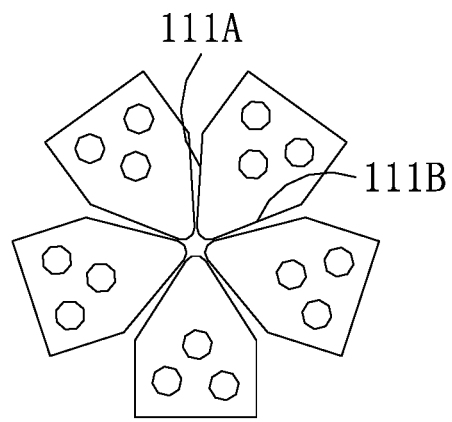

As shown in FIGS. 20 and 21, the driving mechanism 10 of the operating arm 3 has a housing 101. The connecting rod 20 is disposed on the housing 101, and an extending direction of the connecting rod 20 is tangent to the side surface 111 of the housing 101, thereby enabling the connecting rods 20 of the plurality of operating arms 3 to extend into a human body via one incision. Wherein the side surface 111 of the housing 101 is a surface connected to the bottom surface 112. The bottom surface 112 is the surface facing toward the human body. The end effector 40 and/or the connecting unit assembly 30 may also be omitted according to actual needs.

In this embodiment, the connecting rod 20 is substantially a rigid connecting rod. During the installation process of the operating arm 3, the connecting rod 20 is directly disposed on the power mechanism 2 without bending the connecting rod 20. In another embodiment, the connecting rod 20 can also be a flexible connecting rod. Alternatively, the connecting rod 20 can also be omitted, and the connecting unit assembly 30 is directly connected to the driving mechanism 10. Since the connecting rod 20 is tangent to the housing 101, the connecting rods 20 of the plurality of operating arms 3 can extend into the human body via one incision, which can reduce the distance between each two of the driving mechanisms 10 of the plurality of operating arm 3 driving mechanisms 10, enables the plurality of operating arms 3 to be more compact, and reduces the volume of the area of the power mechanism for mounting the operating arm 3. In addition, the connecting rod 20 is a rigid connecting rod 20, which makes the surgical procedure to be more stable.

The housing 101 has a first side surface 111A and a second side surface 111B adjacent to the first side surface 111A for abutting against a first side surface 111A or a second side surface 111B of the adjacent operating arm 3, thereby enabling the plurality of operating arms 3 to be distributed about a central axis. Alternatively, the first side surface 111A and the second side surface 111B of one operating arm 3 are arranged adjacent to the first side surface 111A or the second side surface 111B of the adjacent operating arm 3, so that the plurality of operating arms 3 is distributed about a central axis. For example, the first side surface 111A of one of the two adjacent housings 101 is opposite to the first side surface 111A or the second side surface 111B of the other housing 101, and there is a gap between the oppositely disposed surfaces. There is an acute angle formed between the first side surface 111A and the second side surface 111B. In another embodiment, there is a right angle or an obtuse angle formed between the first side surface 111A and the second side surface 111B.

Moreover, the edge of the first side surface 111A extends to the edge of the second side surface 111B to enable the two side surfaces 111 to be connected to each other, and the connection part of them is a curved surface. Wherein the connecting rod 20 is tangent to the curved surface. In one embodiment, the curvature radius of the curved surface is substantially equal to the radius of the connecting rod 20. In another embodiments, the curvature radius of the curved surface may also be different from the radius of the connecting rod 20. Alternatively, in other embodiment, as shown in FIGS. 22-28, the connecting rod may not be disposed on an adjacent part of the plurality of sides.

In another embodiment, the housing may be another shape. In the embodiment shown in FIGS. 4 and 22, the housing is rectangular. In the embodiment shown in FIGS. 23-26, the housing 101 has a first main body 343. The first main body 343 has a mounting surface 344 for connecting to the power mechanism 2 (shown in FIG. 2). A second main body 345 extends from the mounting surface 344, and the free end of the second main body 345 protrudes from the mounting surface 344. The second main body 345 and the first main body 343 forms a notch 36 for receiving the power mechanism 2, wherein the free end is an end portion extending out of the first main body 343 and not connected to the first main body 343. In FIGS. 23-25, the second main body extends along one edge of the mounting surface to enable the housing to be L-shaped. In FIG. 26, the second main body extends from the middle part of the mounting surface to enable the housing to be T-shaped and to have two notches 36. It is noted that, in different embodiments, the regions of the housing connected to the connecting rods may be in the same manner as the embodiment shown in FIG. 20 and FIG. 21. For example, the second body has a first side surface, a second side surface adjacent to the first side surface, both for abutting against the first side surface or the second side surface of the adjacent operating arm. Alternately, the first side surface and the second side surface of the housing is used for keeping a gap from the first side surface or the second side surface of the adjacent operating arm, thereby enabling the plurality of operating arms to be distributed about a central axis.

Figure 22:
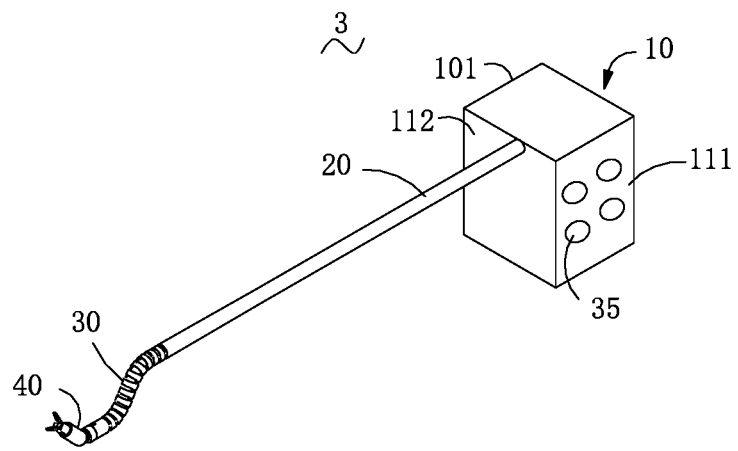
Figure 23:
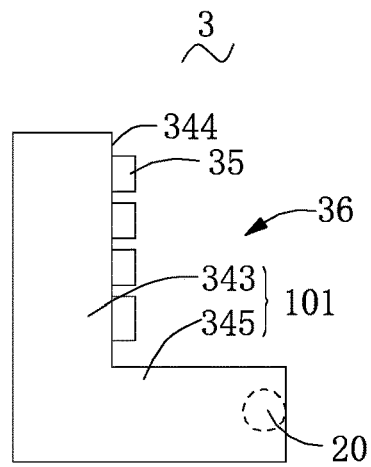
Figure 24:
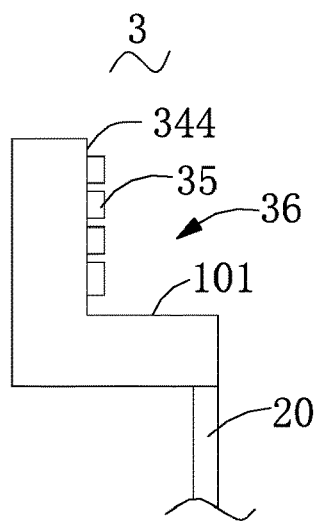
Figure 25:
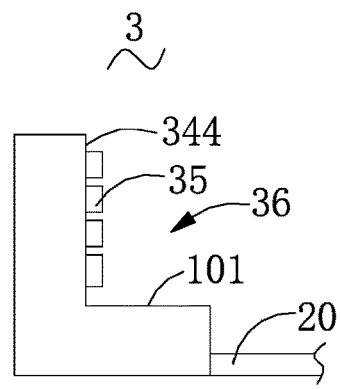
Figure 26:
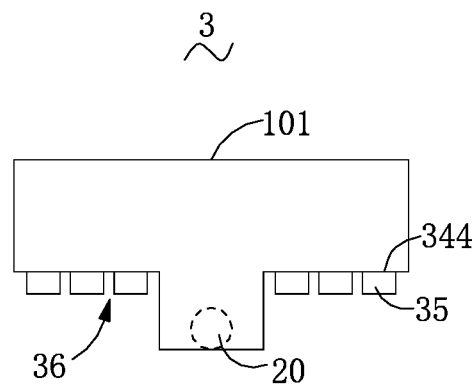

As shown in FIGS. 4 and 20-26, the surface of the housing for connecting to the power mechanism and the surface of the housing for connecting to the connecting rod may have various position relationships. The connecting rod may be disposed on any surface of the housing, such as a side surface, a bottom surface, and a surface opposite to the bottom surface. The connecting rod may be disposed adjacent to the side surface and not tangent to the side surface. As shown in FIG. 4, the surface of the housing 101 for connecting to the power mechanism and the surface for connecting to the connecting rod 20 are the same surface. Specifically, there is a connecting plate placed on the bottom surface 112 of the housing 101 for connecting to the power mechanism, and the connecting rod 20 is disposed on the bottom surface 112 of the housing 101. As shown in FIG. 20, the surface of the housing 101 for connecting to the power mechanism is opposite to the surface for connecting to the connecting rod 20. Specifically, the connecting rod 20 is disposed on the bottom surface 112 of the housing 101 and adjacent to the edge part of the bottom surface 112. The surface of the housing 101 opposite to the bottom surface 112 is used for connecting to the power mechanism. As shown in FIG. 22, the surface of the housing 101 for connecting to the power mechanism may also be disposed adjacent to the surface for connecting to the connecting rod 20, that is, one side surface 111 of the housing 101 is used for connecting to the power mechanism, and the connecting plate is disposed on the second main body. In FIGS. 23, 24, and 26, the mounting surface 344 is parallel to the connecting rod 20. In FIG. 25, the mounting surface 344 is perpendicular to the connecting rod 20. In FIGS. 23, 25, and 26, the notch 36 is located in the extending direction of the side surface of the second main body. In FIG. 24, the notch 36 is located in the extending direction of the surface of the second main body opposite to the bottom surface. Specifically, the connecting rod 20 is disposed on an area of the second main body 345 adjacent to the free end of the second main body 345. For example, the connecting rod 20 is disposed on the bottom surface of the second main body and is tangent to the side surface of the second main body in the extending direction of the connecting rod 20. Wherein the bottom surface of the second main body is a surface facing toward the human body during the surgical operation, and the side surface is a surface adjacent to the bottom surface. A connecting plate 35 is disposed on the mounting surface 344 for connecting to the power mechanism 2.

In one embodiment, the connecting rod 20 is a straight rod, and the connecting rod 20 is rotatably disposed on the housing 101 of the driving mechanism 10. The driving mechanism 10 drives the connecting rod 20 to rotate along the axis of the connecting rod 20. In another embodiment, the connecting rod 20 may also be a non-straight rod. Alternatively, the connecting rod 20 may be fixedly disposed on the housing 101.

Figure 27:
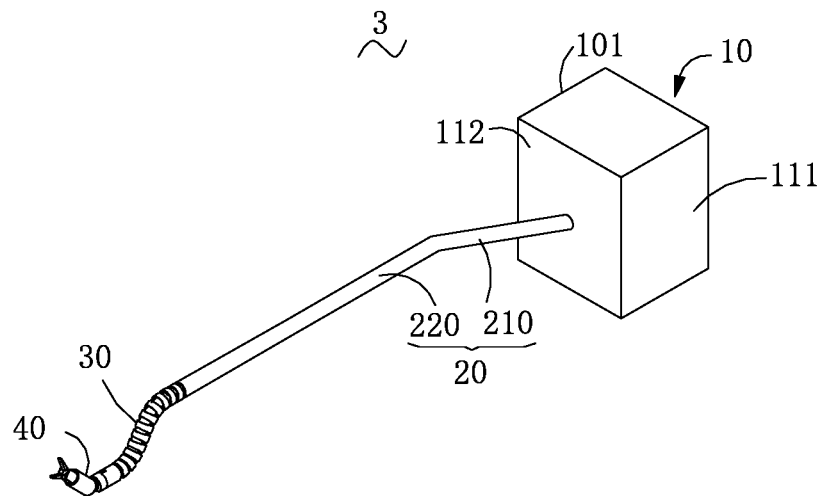

As shown in FIG. 27, in one embodiment, the connecting rod 20 includes a first connecting rod 210 and a second connecting rod 220 which are sequentially connected. Wherein the first connecting rod 210 is disposed on the housing 101 and is fixedly connected to the second connecting rod 220. An angle is formed between the first connecting rod 210 and the second connecting rod 220, and the angle is a non-straight angle. In the present embodiment, the second connecting rod 220 is tangent to the side surface 111 of the housing 101, and the connecting rod 20 is fixedly disposed on the housing 101. At this time, the end effector 40 connected to the connecting rod 20 may rotate relative to the connecting rod 20, thereby ensuring the degree of freedom of the operating arm 3. In another embodiment, the second connecting rod may be not tangent to the housing, and the second connecting rods of the plurality of operating arms are required to extend into the human body via one incision.

The first connecting rod may also be rotatably disposed on the housing. For example, the first connecting rod is a flexible rod or the flexible pipe, or the first connecting rod is connected to the second connecting rod via the flexible joint assembly, thereby enabling the positions of the first connecting rod and the second connecting rod to be adjusted. The second connecting rods pass through the trocar or the sleeve and the positions of the second connecting rods are limited relative to the human body. The first connecting rod drives the second connecting rod to rotate about the fixed rotating axis, that is, the rotating axis of the second connecting rod does not change when the first connecting rod is bent. As another example, the second connecting rod is fixed relative to the position of the first connecting rod, and at the moment, the first connecting rod and the second connecting rod are connected via the transmission mechanism, so that when the first connecting rod rotates, the second connecting rod is driven to rotate about the fixed rotating axis. The first connecting rod may be located in a middle region of the surface of the housing when the first connecting rod is rotatably disposed on the housing. It should be noted that when the first connecting rod is a flexible rod or the flexible pipe, or the first connecting rod can be fixedly connected to the housing when the first connecting rod is connected to the second connecting rod via the flexible joint assembly. At this time, the end effector connected to the connecting rod can rotate relative to the connecting rod.

Figure 28:
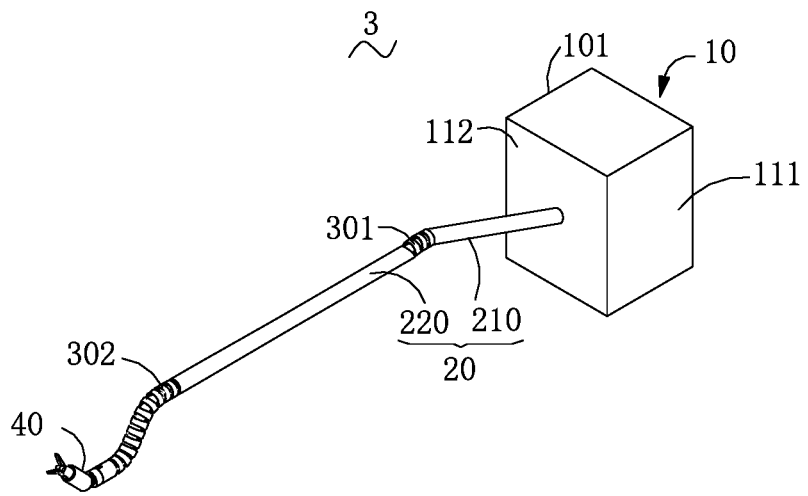

As shown in FIG. 28, in one embodiment, the connecting rod 20 includes a first connecting rod 210 and a second connecting rod 220. The connecting unit assembly 30 includes a first connecting unit assembly 301 and a second connecting unit assembly 302. The first connecting rod 210 is disposed on the driving mechanism 10 and is in swinging connection with the second connecting rod 220 via the first connecting unit assembly 301. The second connecting rod 220 is used for connecting to the end effector 40 or the second connecting unit assembly 302. When the second connecting rod 220 is connected to the second connecting unit assembly 302, the end effector 40 is connected to the distal end of the second connecting unit assembly 302. In a surgical operation, the first connecting unit assembly 301 is located out of the human body, and the second connecting unit assembly 302 is located in the human body. It should be noted that, in the present embodiment, the second connecting rod 220 is tangent to the side surface 111 of the housing 101. In another embodiment, the second connecting rod 220 may also be not tangent to the housing 101 and has another position relationship with the housing 101. The operating arm drives the connecting unit assembly 30 via the driving mechanism 10 to swing the second connecting rod 220 relative to the first connecting rod 210, thereby adjusting the position of the second connecting rod 220 and the end effector 40 connected to the second connecting rod 220, which fully utilizes the space between the driving mechanism 10 of the operating arm 3 and the human body, and improves the flexibility of the operating arm 3.

In one embodiment, there is a plurality of the first connecting rod, and the plurality of first connecting rods is sequentially in a swing connection via the first connecting unit assembly. The first connecting rod located at the proximal end is connected to the driving mechanism, and the first connecting rod at the distal end is connected to the second connecting rod through the first connecting unit assembly, which further improves the flexibility of the operating arm.

Moreover, at least two connecting unit assemblies 30 of the plurality of connecting unit assemblies 30 are coupled to each other, and the coupled connecting unit assemblies 30 correspondingly rotate according to the coupling relationship. Specifically, in one embodiment, at least two first connecting unit assemblies 301 are coupled to each other. when the coupled first connecting unit assemblies 301 rotate, the pose of the connecting rod located at the distal end of the first connecting unit assembly 301 remains unchanged, that is, the pose of the first connecting rod 210 or the second connecting rod 220 connected to the first connecting unit assembly 301 remains unchanged. For example, there is a plurality of the first connecting rod 210, the first connecting rod 210 located at the distal end is connected to the second connecting rod 220 and another first connecting rod 210 by two coupled first connecting unit assemblies 301 respectively. When the coupled first connecting unit assemblies 301 rotate, the second connecting rod 220 remains in parallel with the other first connecting rod 210 connected to the first connecting rod 210 located at the distal end. In another embodiment, when the first connecting unit assembly 301 is coupled to the second connecting unit assembly 302, the pose of the distal end of the second connection assembly 302 remains unchanged when the coupled connecting unit assembly 30 rotates. In the above embodiments, a sum of the rotation angles of the coupled connecting unit assemblies in each direction are substantially the same when the coupled connecting unit assemblies rotate. In another embodiment, the coupled connecting unit assemblies 30 may also rotate in the same direction, for example, the rotation angles of the coupled connecting unit assemblies 30 are proportional.

In the present embodiment, the sum of the rotation angles of each of the joint assemblies of the coupled connecting unit assemblies is substantially the same to ensure that the pose of the connecting unit located at the distal end remains unchanged when the coupled connecting unit assembly is bent and swings. Wherein each joint assembly of a coupled connecting unit assembly is correspondingly coupled. For example, two first connecting unit assemblies are coupled, wherein each first connecting unit assembly has a joint assembly, the rotation directions of the two joint assemblies are opposite, and the rotation angles of them are the same. As another example, two first connecting unit assemblies are coupled, each of the two first connecting unit assemblies includes two joint assemblies, wherein two joint assemblies of one of the two connecting unit assemblies are coupled to two joint assemblies of another one of the two connecting unit assemblies. As another example, each of the joint assemblies of the coupled connecting unit assembly may also rotate in the same direction, and the rotation angles are proportional. It should be noted that the joint assembly can be a driving joint assembly or a driven joint assembly. The driving joint assembly is a joint assembly that rotates by a drive mechanism, and the driven joint assembly is a joint assembly that follows a rotation when the driving joint assembly rotates.

Figure 29:
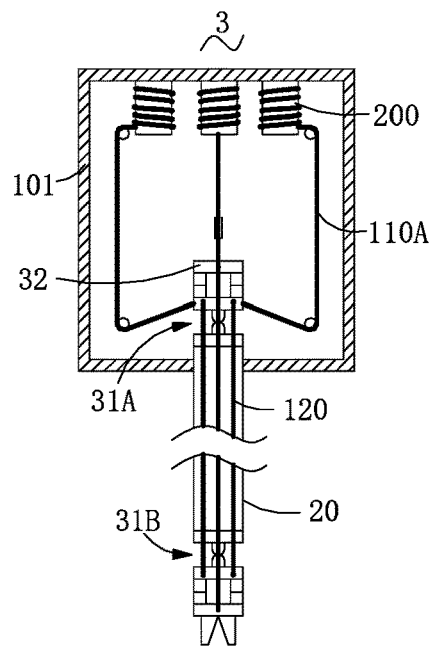

Please refer to FIG. 29, in one embodiment, the operating arm includes a driving mechanism, a connecting rod, a connecting unit assembly, and an end effector, and they are connected sequentially. the joint assembly includes a first driving joint assembly 31*a* and a driven joint assembly 31*b* coupled to each other. When the first driving joint assembly 31*a* is bent, the driven joint assembly 31*b* is bent correspondingly according to the coupling relationship. The first driving joint assembly 31*a* is located in the housing 101. The driven joint assembly 31*b* is located out of the housing 101 and is connected to the distal end of the connecting rod 20. That is, the connecting rod is located between the first driving joint assembly and the driven joint assembly. The above operating arm controls the first driving joint assembly located in the driving mechanism to drive the driven joint assembly located out of the driving mechanism 10, thereby enabling the control to be more accurate.

The driving mechanism further includes a driving portion 200 and driving wires 100 disposed in the housing 101. The driving portion is used for driving the connecting unit assembly. The driving wires includes a master driving wire and a slave driving wire 120. Wherein one end of the master driving wire is disposed on the driving portion 200, and the other end of the master driving wire is disposed on the joint assembly 31*a* to drive the driving joint assembly to rotate. For example, one end of the master driving wire is disposed on a connecting unit of the joint assembly driven by the master driving wire; and as another example, the master driving wire is disposed on a connecting unit located at the distal end of the joint assembly driven by the master driving wire. Wherein the driving joint assembly drives the rest of the joint assembly, between the joint assembly driven by the master driving wire and the joint assembly located at the proximal end, to move. One end of the slave driving wire 120 is disposed on the driven joint assembly 31*b* driven by the slave driving wire 120, and the other end of the slave driving wire 120 is disposed on the first driving joint assembly 31*a* which drives the driven joint assembly 31*b* to rotate, thereby enabling the driven joint assembly to rotate when the first driving joint assembly rotates. It should be noted that the slave driving wire 120 may also be disposed on other joint assemblies. For example, the distal end of the slave driving wire is disposed on the joint assembly located at the distal end of the driven joint assembly. In FIG. 29, the first master driving wire 110A for driving the first driving joint assembly 31A is located in the housing 101 and is connected to the connecting unit 32 of the first driving joint assembly 31A. It is also understood that the first master driving wire of the first driving joint assembly does not pass through other connecting units. The first master driving wire is only disposed on the connecting unit driven by the first master driving wire and drives the first driving joint assembly from the outside of the connecting unit assembly. Moreover, each of the connecting units in the first driving joint assembly is driven by a first master driving wire, ie, each connecting unit in the first driving joint assembly is connected to the first master driving wire. In the embodiment, the first driving joint assembly is driven by two first master driving wires, and the two first master driving wires are connected to connecting units of the first driving joint assembly from opposite sides to drive the first driving joint assembly to rotate clockwise or counterclockwise. The two first master driving wires are located on the same connecting unit of the first driving joint assembly, or are respectively located on two connecting units of the first driving joint assembly. It should be noted that the fixed connecting unit of the first driving joint assembly does not need to be provided with a driving wire, and only one other connection unit of the joint assembly needs to be driven when the first driving joint assembly with the connecting unit is driven to rotate. Wherein the fixed connecting unit will be described below.

In other embodiments, the first master driving wire is replaced with a connecting rod. For example, the driving mechanism includes a driving rod driven by a driving portion. The driving rod is connected to at least one connecting unit of the first driving joint assembly to drive the driving joint assembly to rotate. At this time, only one driving rod is disposed on each connecting unit. For example, there is a cam mechanism located between the driving portion and the driving rod, in particular, the driving portion is connected to the cam, so that the cam rotates with the driving portion, and the driving rod abuts against the surface of the cam and moves along the straight line to drive the connecting unit connected to the driving rod. As another example, there is a gear rack mechanism located between the driving portion and the driving rod, in particular, the driving portion is connected to a gear, so that the gear rotates with the driving portion, and the driving rod is provided with a rack matched with the gear so as to drive the connecting unit connected to the driving rod.

Figure 30:
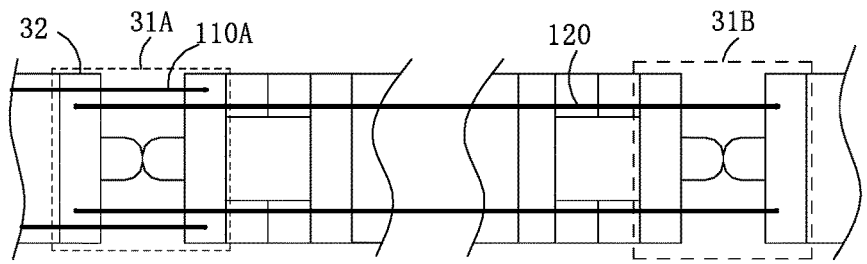
FIG. 30 is a structural schematic view of a connecting unit assembly.

As shown in FIG. 30, the first master driving wire 110*a* of the first driving joint assembly 31*a* is driven to pass through the first driving joint assembly 31*a* and is connected to the connecting unit 32 of the first driving joint assembly driven by the first driving joint assembly 31*a*. It is also understood that the first master driving wire passes through each connecting unit between the driving portion and the first driving joint assembly driven by the driving portion, and the first master driving wire drives the first driving joint assembly in the connecting unit assembly.

Figure 31:
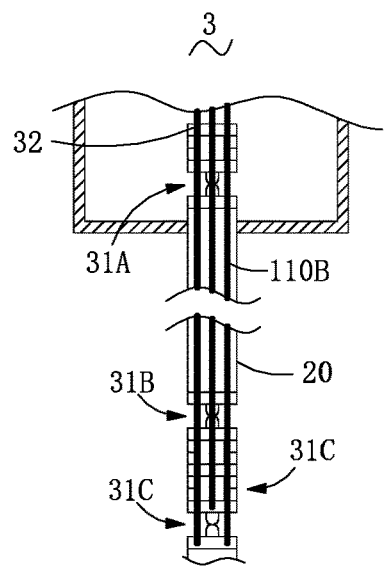
Figure 32:
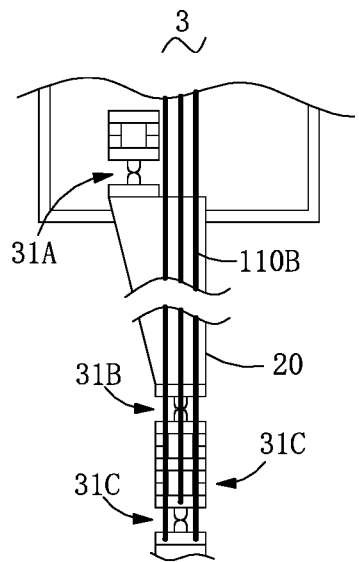

As shown in FIGS. 31 and 32, in addition to the above structure, the connecting unit assembly 30 of the operating arm further includes a second driving joint assembly 31c located out of the driving mechanism 10 driven by the second master driving wire 110b. As shown in FIG. 31, the second master driving wire 110b passes through the first driving joint assembly 31a and extends to the second driving joint assembly 31c driven by the second master driving wire 110b. As shown in FIG. 32, the second master driving wire 110b is located out of the first driving joint assembly 31a, ie, the movement of the first driving joint assembly does not affect the movement of the second master driving wire.

The second driving joint assembly may be located at the proximal end of the driven joint assembly, or may be located at the distal end of the first follower joint. Alternatively, when there is a plurality of the driven joint assemblies and/or the second driving joint assemblies, the driven joint assemblies and the second driving joint assemblies are crossed. Specifically, the distal end of the driven joint assembly 31b is connected to the second driving joint assembly 31c, and the proximal end is connected to the connecting rod 20. In other embodiments, the proximal end of the second driving joint assembly 31c can also be connected to the connecting rod 20, and the distal end is connected to the driven joint assembly 31b. At this time, the second driving joint assembly 31c and the first driving joint assembly 31a are both coupled to the driven joint assembly 31b, ie, the movement of the second driving joint assembly 302c drives the driven joint assembly 302b to move accordingly.

It should be noted that the connecting unit assembly may include a plurality of sets of joint assemblies, the rotation axis of the joint assembly in each set is different, so that the connecting unit assembly has a plurality of degrees of freedom. For example, there are two sets of first driving joint assemblies, the rotation axes of the two sets of first driving joint assemblies are orthogonal. At this time, the driven joint assembly is set corresponding to the first driving joint assembly. Each joint assembly may also have at least two degrees of freedom, which makes the joint assembly more flexible.

As shown in FIGS. 29-32, The connecting rod 20 is communicated with the distal end of the first driving joint assembly 31a so that the connecting rod 20 passes through the two ends of the slave driving wire 120 and is connected to the driving joint assembly 31a and driven joint assembly 31b. The driving joint assembly 31a and driven joint assembly 31b are coupled and connected to the two opposite ends of the connecting rod 20. At this time, the distal end of the first driving joint assembly 31a is fixed to the housing, ie, the connecting unit located at the distal end of the first driving joint assembly 31a is a fixed connecting unit, and the proximal end of the first active joint assembly is a free end and is not connected to other components.

In other embodiments, the connecting rod may also be spaced apart from the first driving joint assembly. At this time, the proximal end of the first driving joint assembly is fixedly disposed in the housing, the proximal end of the first driving joint assembly is a fixed connecting unit, and the distal end of the first driving joint assembly is a free end and is located on an opposite side relative to the connecting rod. A slave driving wire extends from the first active joint assembly into the connecting rod and is disposed on a joint assembly driven by the slave driving wire.

As shown in FIGS. 31 and 32, the connecting unit assembly includes a second driving joint assembly, the second master driving wire, for driving the second driving joint assembly to rotate, passes through the connecting rod, and extends to the driven joint assembly. In FIG. 31, the second master driving wire 110b and the slave driving wire pass through the connecting rod 20 via the same area of the connecting rod 20. In FIG. 32, the second master driving wire 110b and the slave driving wire pass through the connecting rod 20 via different areas of the connecting rod 20.

In one embodiment, the connecting rod is fixedly disposed on the housing of the driving mechanism. At this time, the first driving joint assembly is fixedly connected to the connecting rod. In other embodiments, the connecting rod can be rotatably disposed on the driving mechanism along the axial direction of the connecting rod. At this time, the first driving joint assembly is fixedly disposed on the housing, the connecting rod passes through the housing and communicates with the first driving joint assembly. That is, the first driving joint assembly does not rotate with the connecting rod.

Figure 33:
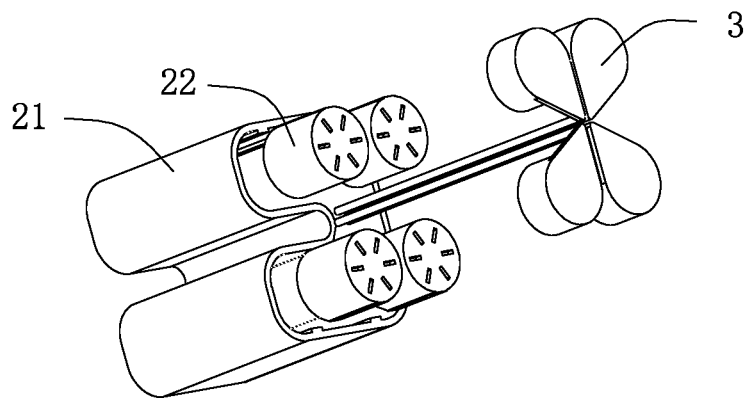
FIGS. 33, 35, and 37 are exploded and structural schematic views of different embodiments of a part of the operating arm.
Figure 34:
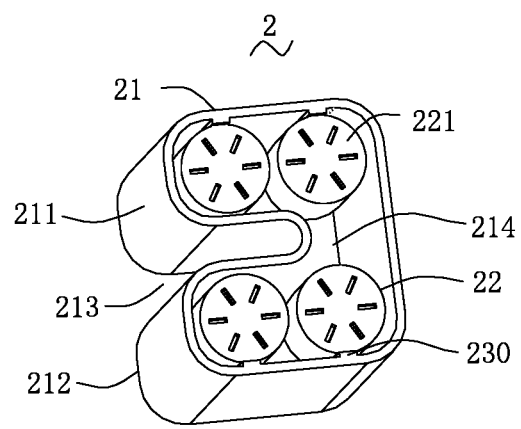
FIGS. 34, 36, and 38-39 are structural schematic views of different embodiments of the operating arm.

As shown in FIGS. 33 and 34, the power mechanism 2 includes a body 21 and a power portion 22, wherein a mounting groove 213 is formed in the side surface 211 of the body 21, the mounting groove 213 passes through the bottom surface 212 of the body 21 to enable the operating arm 3 to slide along the side surface 211 to move into the mounting groove 213. The distal end of the mounting groove 213 is located out of the mounting groove 213, that is, the end effector of the operating arm 3 is basically located out of the mounting groove 213 in the mounting process. The end effector does not need to pass through the mounting groove 213 to extend out of the mounting groove 213. The power portion 22 is disposed on the body 21 for connecting to the driving mechanism of the operating arm 3 and provides power to the operating arm 3 to enable the operating arm 3 to perform a corresponding operation. For example, the operation refers to changing the position or pose of the end effector. Wherein the bottom surface 212 of the body 21 faces toward the patient during the operation process, and the side surface 211 is a surface adjacent to the bottom surface 212. When the operating arm is installed, the operating arm moves into the mounting groove 213 through the opening of the side surface 211 of the body 21. At this time, the mounting groove 213 passes through the bottom surface 212 of the body 21, the operating arm 3 moves into the mounting groove 213 and is not blocked by the bottom surface 212. After the operating arm 3 is located in the mounting groove 213, the operating arm 3 is connected to the power portion 22. It is simpler and faster for installing the operating arm 3 of the slave operating device of the power mechanism 2 described above.

In the embodiment, there is one mounting groove and there is a plurality of power portions. Each power portion is connected to the corresponding operation arm. The plurality of operating arms, connected to the power portion, passes through the mounting grooves so that the plurality of operating arms can extend into the human body via one incision. In other embodiments, the power mechanism may also have only one power portion. Alternatively, at least two operating arms pass through the mounting groove. For example, a part of the operating arm is disposed in the human body and passes through the mounting groove, thereby enabling the end to extend out of the body. A part of the operating arm is disposed on the outer side of the body and does not pass through the mounting groove. In addition, there may be a plurality of mounting grooves. For example, there are two mounting grooves. Wherein two operating arms are received in the at least one mounting groove, and the rest operating arms are received in the other mounting groove. At this time, the plurality of mounting grooves may be defined on the same side surface or different side surfaces of the body. For example, the plurality of mounting grooves is defined in two opposite side surfaces of the body. A plurality of operating arms extends into the human body via two incisions. Each incision corresponds to a mounting groove. The operating arm extends out of the mounting groove and extends into the corresponding incision. When there is a plurality of grooves, and at least two of the mounting grooves may correspond to one incision. That is, an operating arm extends out of the plurality of mounting grooves corresponding one incision and extends into the incision. Alternatively, a plurality of operating arms extending out of the same mounting groove and extends into the human body via the plurality of incisions.

The body 21 further defines a receiving groove 214 for receiving the power portion 22. The operating arm moves to enable the connecting rod to move along the side surface of the body to move into the mounting groove during the installation process of the operating arm, thereby enabling the driving mechanism of the operating arm to move close to the power portion in the receiving groove. And then the driving mechanism is connected to the corresponding power portion.

In the embodiment shown in FIGS. 33 and 34, the surface of the body 21 defining the receiving groove 214 is opposite to the bottom surface 212. The mounting groove 213 passes through the bottom surface of the receiving groove 214. That is, the mounting groove 213 passes through the bottom surface of the receiving groove 214 and the bottom surface 212 of the body 21 along the extending direction of the connecting rod 20 of the operating arm 3, so that the operating arm 3 can be installed to the body 21 along the side surface of the body 21. The power portion 22 is received in the receiving groove 214, and the connecting surface 221 for connecting to the operating arm 3 is the surface of the power portion 22 opposite to the bottom surface 212 of the body 21. At this time, the surface of the power portion 22 for connecting to the operating arm is the surface of the driving mechanism facing toward the bottom surface 212. For example, when the operating arm shown in FIG. 4 is installed, the operating arm moves toward the bottom surface 212 to engage with the connecting surface 221.

Figure 35:
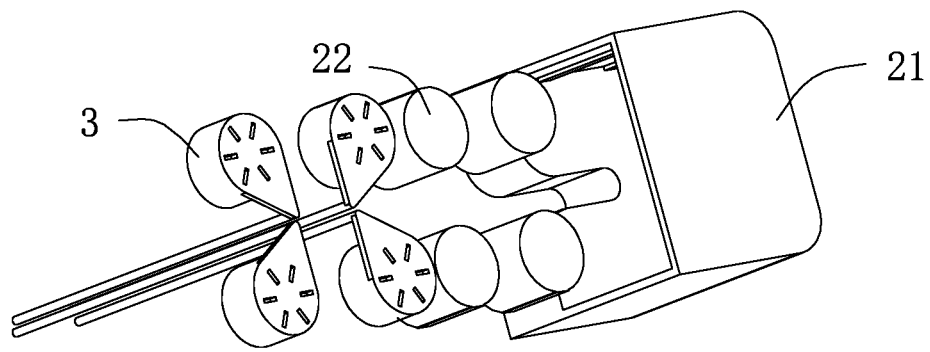
Figure 36:
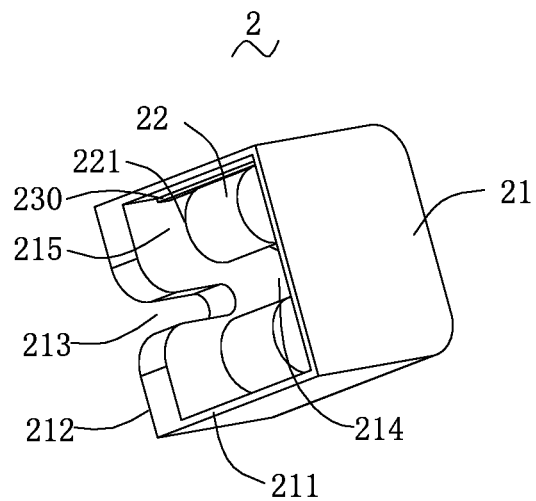

In the embodiment shown in FIGS. 35 and 36, the surface of the body 21 defining the receiving groove 214 is the same as the surface defining the mounting groove 213. That is, the opening of the receiving groove 214 is located in the side surface 211 of the body 21, and the mounting groove 213 passes through the first inner wall 215 of the receiving groove 214 adjacent to the bottom surface of the body 21, so that the connecting rod of the operating arm can pass through the mounting groove and extend out of the body 21. The power portion 22 is disposed in the receiving groove 214 and is spaced apart from the first inner wall 215 to form the receiving area for receiving the power portion 22. The connecting surface 221 of the power portion 22 connected to the operating arm 3 is a surface of the power portion 22 facing toward the bottom surface 212 of the body 21. At this time, the surface of the power portion 22 connected to the operating arm 3 is opposite to the bottom surface of the driving mechanism. For example, when the operating arm shown in FIG. 20 is installed, the operating arm moves toward the bottom surface 212 to engage with the connecting surface 221.

Figure 37:
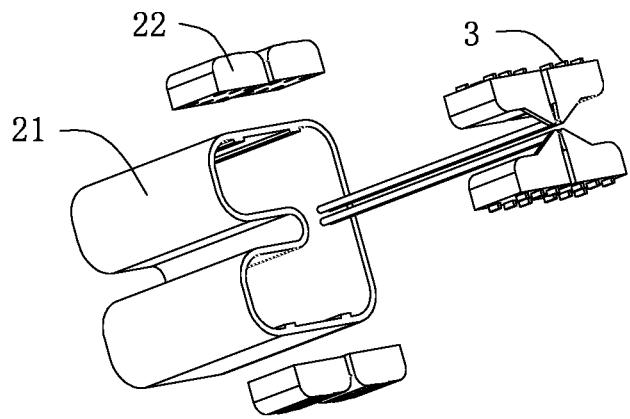
Figure 38:
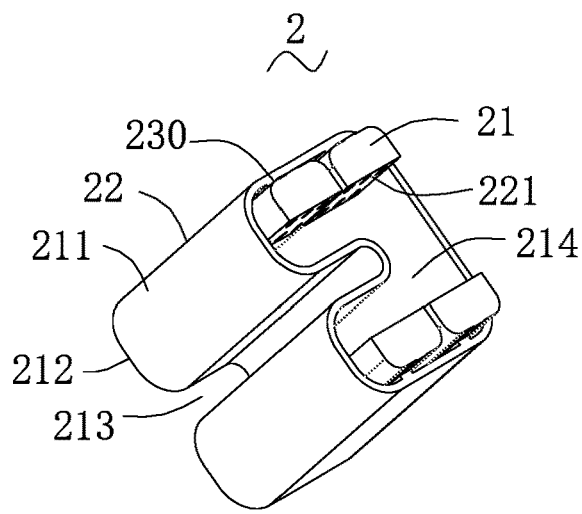

In the embodiment shown in FIGS. 37 and 38, the surface of the body 21 defining the receiving groove 214 is opposite to the bottom surface 212. The mounting groove 213 extends through the bottom surface of the receiving groove 214. The power portion 22 is disposed in the mounting groove 213. The connecting surface 221 of the connecting operating arm 3 is the surface of the power portion 22 facing toward the side surface of the body 21, and the connecting surface 221 faces toward the middle portion of the body, such as the middle portion of the receiving groove 214. At this time, the surface of the power portion connected to the operating arm 3 is a side surface of the driving mechanism. For example, the operating arm is the operating arm of the embodiment shown in FIG. 22, and when the operating arm is installed, the operating arm moves toward the connecting surface 221 to engage with the connecting surface 221.

Figure 39:
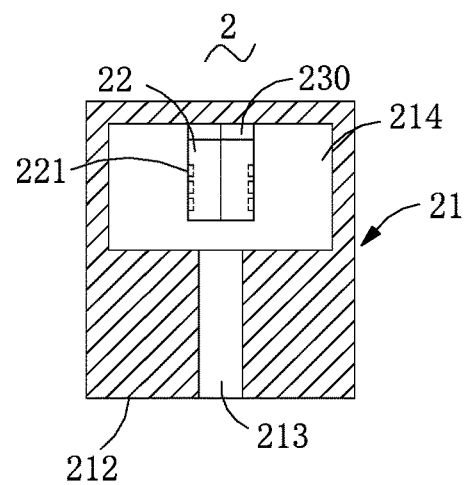

The embodiment shown in FIG. 39 is similar to the embodiment shown in FIGS. 37 and 38. At this time, the power portion 22 is located in the middle part of the receiving groove 214, and the connecting surface 221 faces toward the side surface of the body. For example, the connecting surface 221 faces toward the side surface of the receiving groove. The surface of the body defining the receiving groove is the same as the surface defining the mounting groove. For example, the operating arm 3 of the embodiment shown in FIG. 23, FIG. 24, and FIG. 26, at this time, the power portion 22 is partially received in the notch of the housing of the driving mechanism, and the plurality of operating arms may extend into the human body via one incision since the connecting rods are located in the region of the bottom portion of the driving mechanism. It should be noted that the surface of the body defining the receiving groove may also be opposite to the bottom surface.

In each of the above embodiments, the receiving groove 214 of the body 21 may also be omitted. At this time, the power portion 22 is disposed out of the body 21. For example, the power portion 22 is disposed on a surface opposite to the bottom surface 212.

Moreover, the power portion 22 is slidably mounted to the body 21. As shown in FIGS. 33-39, the receiving groove 214 is defined in the guide rail 230, and the power portion 22 is slidably mounted to the guide rail 230. In one embodiment, the operating arm moves along with the power portion, that is, the sliding direction of the power portion 22 is the same as the extending direction of the mounting groove 213. In other embodiments, the sliding direction of the power portion may be other directions to adjust the position of the operating arm. For example, the sliding direction of the power portion is perpendicular to the extending direction of the mounting groove.

Figure 40:
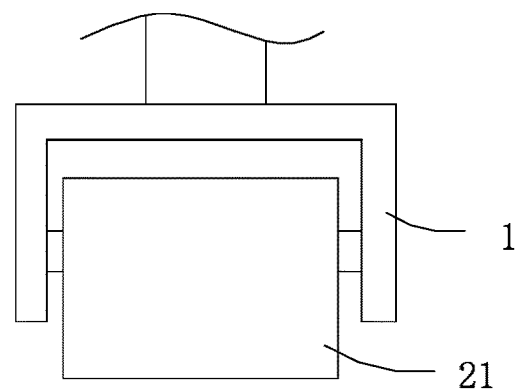
FIG. 40 is a structural schematic view of an embodiment of a part of the slave operating device.

As shown in FIG. 40, in one embodiment, the body 21 of the power mechanism 2 is rotatably mounted to the mechanical arm 1. Specifically, the end portion of the mechanical arm is in the shape of "pi", and is rotatably connected to two opposite surfaces of the body 21. The surface of the body rotatably connected to the mechanical arm is different from the surface of the body defining the mounting groove. Moreover, the end portion of the mechanical arm has a motor for driving the body to rotate. In the embodiment, there is only one motor located on one side of the body. In other embodiments, there are two motors located on both sides of the body. It should be noted that the end portion of the mechanical arm can also be rotatably connected to one surface of the body, and the surface can be the same as the surface of the body defining the mounting groove and can be different from the surface of the body defining the mounting groove. For example, the surface is adjacent to the surface of the body defining the mounting groove. At this time, when the end portion of the mechanical arm has a motor, the motor is located on one side of the mechanical arm connected to the body.

In one embodiment, the rotation angle of the power mechanism 2 relative to the mechanical arm is 0 to 360 degrees. In this way, the operating arm 3 connected to the power portion 22 is more easily adjustable. In other embodiments, the rotation angle of the power mechanism 2 relative to the mechanical arm may also be other angles, such as 0 to 180 degrees, 0 to 90 degrees, etc.

The various technical features of the above-described embodiments may be combined in any combination, so that the description is concise, and all possible combinations of the various technical features in the above-described embodiments are described. However, as long as the combination of these technical features does not conflict, it is to be understood that the scope of the present specification is not to be taken in a limiting sense.

The above-described embodiments have only expressed several embodiments of the present application, which are described in more detail and detail, but are not therefore to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

What is claimed is:

1. A power mechanism of a surgical system, comprising:
a plurality of operating arms
   a body, a side surface of the body defining a mounting groove, the mounting groove passing through a bottom surface of the body to enable at least two of the plurality of operating arms to move from the side surface to the mounting groove, and a distal end of each of the at least two of the plurality of operating arms located out of the mounting groove; and
   a plurality of power portions disposed on the body for connecting to the plurality of operating arms and providing power for the plurality of operating arms, wherein the plurality of power portions connects to the plurality of operating arms respectively, and the at least two of the plurality of the operating arms pass through the mounting groove.

2. The power mechanism of claim 1, wherein the plurality of the operating arms, connected to the plurality of power portions, pass through the mounting groove.

3. The power mechanism of claim 1, wherein the plurality of power portions is slidably disposed on the body.

4. The power mechanism of claim 1, wherein the body further defines a receiving groove, the plurality of power portions is received in the receiving groove, a guiding rail is mounted in the mounting groove, and the plurality of power portions is slidably disposed on the guiding rail.

5. The power mechanism of claim 1, wherein the plurality of power portions is received in a receiving groove, and the receiving groove is located on a side of the mounting groove far away from the bottom surface of the body.

6. The power mechanism of claim 1, wherein the body further defines a receiving groove, the plurality of power portions is received in the receiving groove, and a surface of the body, defining the receiving groove, is opposite to the bottom surface of the body.

7. The power mechanism of claim 1, wherein each of the plurality of power portions comprises a connecting surface connected to a respective one of the plurality of operating arms, the connecting surface is a surface of the power portion facing toward the bottom surface of the body; or the connecting surface is a surface of the power portion facing away from the bottom surface of the body.

8. The power mechanism of claim 1, wherein each of the plurality of power portions comprises a connecting surface connected to a respective one of the plurality of operating arms, the connecting surface is a surface of the power portion extending toward a side surface of the body.

9. The power mechanism of claim 8, wherein the connecting surface extends toward a center area of the body; or the plurality of power portions is located on a center area of the body and the connecting surface extends toward the side surface of the body.

10. A slave operating device of a surgical system comprising:
   a power mechanism, the power mechanism comprising a body and a plurality of power portions, a mounting groove defined in a side surface of the body, the mounting groove passing through a bottom surface of the body, and the plurality of power portions disposed on the body; and
   a plurality of operating arms connected to the plurality of power portions, at least two of the plurality of the operating arms passing through the mounting groove to enable the at least two of the plurality of the operating arms to move from the side surface to the mounting groove, and a distal end of each of the at least two of the plurality of operating arms located out of the mounting groove, wherein the plurality of power portions connects to the plurality of operating arms respectively.

11. The slave operating device of claim 10, wherein the body further defines a receiving groove, and the plurality of power portions is received in the receiving groove.

12. The slave operating device of claim 10, wherein the body further defines a receiving groove, and the plurality of power portions is received in the receiving groove; a surface of the body having the receiving groove is opposite of a bottom surface of the body, or the surface of the body having the receiving groove is a side surface of the body having the mounting groove.

13. The slave operating device of claim 10, wherein each of the plurality of power portions comprises a connecting surface connected to a respective one of the plurality of operating arms, the connecting surface is a surface of the power portion extending toward the side surface of the body.

14. The slave operating device of claim 10, wherein each of the plurality of operating arms is disposed on a corresponding one of the plurality of power portions, each of the plurality of operating arms comprises a connecting rod, the connecting rods of the plurality of operating arms are close to each other and pass through the mounting groove of the body.

15. The slave operating device of claim 10, wherein each of the plurality of operating arms comprises an enclosure and a connecting rod, the connecting rod is disposed on the enclosure, the connecting rod is substantially a rigid connecting rod, and is tangent to a side surface of the enclosure in an extending direction of the connecting rod, thereby enabling the connecting rods of the plurality of operating arms to extend into a human body via an incision.

16. The slave operating device of claim 10, wherein the enclosure comprises a first side surface and a second side surface adjacent to the first side surface, the first side surface and the second side surface of the enclosure are configured to contact a first side surface or a second side surface of an adjacent one of the plurality of operating arms, or are configured to keep a gap from the first side surface or the second side surface of the adjacent one of the plurality of operating arms, thereby enabling the plurality of operating arms to be distributed about a central axis.

17. The slave operating device of claim 10, wherein the slave operating device further comprises a mechanical arm rotatably connected to the body of the power mechanism, a surface of the body connected to the mechanical arm is different from a surface of the body having the mounting groove.

18. The slave operating device of claim 17, wherein a rotating angle of the power mechanism relative to the mechanical arm is from 0 to 360 degrees.

\* \* \* \* \*